United States Patent [19]

Shorter et al.

[11] Patent Number: 5,610,058
[45] Date of Patent: Mar. 11, 1997

[54] CYTOTROPHOBLAST ANTIGEN AND MONOCLONAL ANTIBODIES WHICH SPECIFICALLY BIND CYTOTROPHOBLAST CELLS

[75] Inventors: Simon C. Shorter, Sunnyvale, Calif.; Bernadette L. Ferry; Phyllis M. Starkey, both of Oxford, United Kingdom; Ian L. Sargent, Yarnton, United Kingdom; Christopher W. G. Redman, Oxford, United Kingdom

[73] Assignee: Isis Innovation Limited, Oxford, United Kingdom

[21] Appl. No.: 351,468

[22] PCT Filed: Jun. 8, 1993

[86] PCT No.: PCT/GB93/01212

§ 371 Date: Feb. 23, 1995

§ 102(e) Date: Feb. 23, 1995

[87] PCT Pub. No.: WO93/25664

PCT Pub. Date: Dec. 23, 1993

Related U.S. Application Data

[63] Continuation-in-part of Ser. No. 913,957, Jul. 17, 1992, abandoned.

[30] Foreign Application Priority Data

Jun. 8, 1992 [GB] United Kingdom .................. 9212074

[51] Int. Cl.$^6$ .............................. C07K 16/28; C12N 5/00
[52] U.S. Cl. ........................................ 435/332; 530/388.2
[58] Field of Search ................... 530/350, 388.2, 530/388.85, 389.1, 389.7, 388.8; 435/240.27, 70.21

[56] References Cited

FOREIGN PATENT DOCUMENTS 0412700  2/1991  European Pat. Off. .

OTHER PUBLICATIONS

Goding, Monoclonal Antibodies Principles & Practice, 1986, pp. 125–132, 219–240 Sigma Catalog, pp. 186–187, 193, 1990.

Wild, "Teopholdast Cell Surface Receptors," in Biology of Trophoblast, Loke & Whyte, eds., 1983, Elsevier Science Publishers, pp. 473–479.

Shorter, The Isolation & Characterization of Human Cytotrophoblast pp. 68–69, 212–214, 1989.

Shorter et al., Placenta, vol. 12, No. 4, pp. 434–435 (Jul. 1991).

Mueller et al., The Histochemical Journal, vol. 19, pp. 288–296 (1987).

Loke et al., American Journal of Reproductive Immunology, vol. 27, No. 1/2 (Jan.–Mar. 1992).

Shorter, Dissertation Abstracts International, vol. 52/01–B, p. 170 (1989) (Dialog printout).

Primary Examiner—Frank C. Eisenschenk
Attorney, Agent, or Firm—Wenderoth Lind & Ponack

[57] ABSTRACT

A monoclonal antibody specific for a unique subset of extra-villous trophoblast in human placental tissue, the cell line that produces it, and the isolated antigen to which it is directed.

3 Claims, No Drawings

CYTOTROPHOBLAST ANTIGEN AND MONOCLONAL ANTIBODIES WHICH SPECIFICALLY BIND CYTOTROPHOBLAST CELLS

This is the U.S. national stage of PCT/GB93/01212, which is a continuation-in-part of U.S. application Ser. No. 07/913,957, filed Jul. 17, 1992 now abandoned.

The invention relates to a monoclonal antibody with a unique binding pattern, and the antigen to which the monoclonal antibody binds.

Cytotrophoblast are a cell type unique to the placenta and fetal membranes. In early pregnancy, the extra-villous cytotrophoblast of the cell columns infiltrate the maternal decidua lining the uterus and anchor the placenta [Boyd & Hamilton, 1970], later also invading the maternal spiral arteries as part of a process which allows the hugely increased uteroplacental blood flow required for successful pregnancy [Pijnenborg et al., 1980]. The villous cytotrophoblast covering the chorionic villi fuse and differentiate to form the syncytiotrophoblast which is the major site of exchange of nutrients and waste products between the fetus and the maternal circulation. In the fetal membranes, the extra-villous trophoblast of the chorion are also in direct contact with the maternal decidua [Boyd & Hamilton, 1970].

Trophoblast are known to be heterogeneous, both in function and morphology, but the various trophoblast subsets are poorly defined. Anti-trophoblast antibodies with different specificities are useful for characterising these subsets.

Another use for anti-trophoblast antibodies which may be of significant value commercially is contraception. Monoclonal antibodies could provide a reliable and convenient new method of contraception free of side-effects.

The present invention provides a monoclonal antibody, designated antibody X, raised against a highly purified population of first trimester human cytotrophoblast taken from cell islands, small clumps of extra-villous cytotrophoblast partially covered by syncytiotrophoblast, which are found mainly in first trimester tissue.

In first trimester tissue, antibody X binds to cell island and the interstitial trophoblast invading the maternal decidua. In the second trimester and at term, the antibody labels a subset of cytotrophoblast in the amniochorion. Antibody X does not react with syncytiotrophoblast or villous cytotrophoblast in first trimester placenta, or with term syncytiotrophoblast. The antigen detected by antibody X is specific for cytotrophoblast, and is not present on amniotic epithelium, decidual cells, or villous stromal cells in first trimester or at term. Antibody X does not bind to any normal adult human tissues tested and is not present on breast or cervical carcinoma cells. In relation to other anti-trophoblast antibodies, antibody X defines a unique subset of extra-villous trophoblast, which in the first trimester corresponds to the most invasive forms.

As part of the World Health Organisation 3rd Trophoblast Antigen and Monoclonal Antibody Workshop, 30th Aug. 1992, Rome, Italy, 29 different monoclonal antibodies were tested extensively by participating laboratories for their binding specificities. The final report shows a consensus finding that the monoclonal antibody of the present invention (identified as T77 in the study) is the only human monoclonal antibody with specificity for extra-villous trophoblast and no cross-reactivity with other tissues.

The monoclonal antibody BC-1 of Loke et al. [1992] is also directed at a cell surface antigen expressed by extra-villous cytotrophoblast, but is shown in the WHO Workshop (T93) to cross-react with various human tissues, including other placental cell types.

Further monoclonal antibodies investigated included several from the laboratory of Mueller et al, none of which showed the unique characteristics of monoclonal antibody X. A paper by Mueller et al. [1987] discusses monoclonal antibodies to trophoblast and describes the interest in identifying surface membrane antigens on extra-villous cytotrophoblast cells. There is no disclosure of antibodies with the binding specificity of antibody X, or of the antigen against which antibody X is directed.

The invention also includes a cell line known as cell line X which produces the claimed antibody. Cell line X was deposited under the Budapest Treaty, at the European Collection of Animal Cell Cultures, Porton Down, Salisbury, Wiltshire, UK on 28th May 1992 and has been allocated Accession Number 92052819.

Various techniques are known for taking a hybridoma and preparing additional different hybridomas from the original hybridoma. Such other hybridomas derived from the deposited cell line are considered to be within the scope of the invention. Analogues of monoclonal antibody X which are produced by the different hybridomas are allso considered to be included in the invention.

Part of a monoclonal antibody can sometimes be employed without loss of specificity and could provide advantages in a clinical situation such as easier access to tissues. The invention therefere also covers a portion of the moneclonal antibody, which portion comprises one or more of the Fab fragments of the molecule.

The invention also provides an isolated antigen and variants derived therefrom, capable of binding to anti-trophoblast antibodies including monoclonal antibody X. Techniques for producing variants of antigen molecules are known, and include random and specific methods.

The invention further covers antibodies raised against the above-mentioned isolated antigen or variants thereof, including monoclonal antibodies. Such antibodies may be raised by methods known in the art. The antigen to which monoclonal antibody X binds has been identified as a molecule having a molecular weight of 100 kD. Antigen was isolated from growth medium of the choriocarcinoma cell line BeWo (American Type Culture Collection, 12301 Parklawn Drive, Rockville, Md. 20852). Isolation and characterisation of the antigen will be carried out using known biochemical and molecular biology techniques (see Example 4).

The antibody, alone and in combination with other anti-trophoblast antibodies, will be of use in isolating extra-villous cytotrophoblast and defining their subsets and function. Because of its specificity for invasive forms of cytotrophoblast, it also has the above-noted potential for use in immunological contraception.

EXAMPLES

Example 1

Production of the Cell Line

A detailed description of the isolation of cell island cytotrophoblast and their expression of surface antigens has already been published [Shorter, 1990].

Using a dissecting microscope, cell islands were picked from samples of first trimester chorionic villous tissue from therapeutic abortions. The terminations were for social not medical reasons, and the study was approved by the Central Oxford Regional Ethics Committee. The cells were dispersed by digestion in Dutch modification of RPMI 1640

(DRPMI, Gibco-Europe, Uxbridge, Middlesex, U.K.) supplemented with 1 mM glutamine (Gibco), 50 µg/ml gentamycin (David Bull Laboratories, Warwick, U.K.), 100 µg/ml streptomycin (Glaxo, Greenford, U.K.) and 100 U/ml benzylpenicillin (Glaxo) containing 0.025% trypsin/EDTA (Sigma Chemical Company Ltd., Poole, Dorset BH17 7NH, U.K.) and 1 mg/ml collagenase (Type IV, Sigma) with continuous stirring for 20 min at 37° C. The cells were washed by centrifugation, resuspended in DRPMI and left overnight at 37° C. in 5% $CO_2$ in air to recover, before being used as the immunogen. Labelling of cytospin preparations with JMB2, (gift of Prof. J. O. D. McGee, Nuffield Department of Pathology, Oxford, U.K.) an antibody specific for trophoblast [Redman et al., 1984] showed the cells to be 97% cytotrophoblast.

A balb/c female mouse was immunised with three intraperitoneal injections, at one, four and six weeks, of $10^6$ cell island cytotrophoblast. Three days after the final injection, spleen cells were removed, a single cell suspension prepared by gentle mechanical disaggregation, and $10^8$ spleen cells and $2\times10^7$ P3-NSI myeloma cells were fused with 50% polyethylene glycol 1500 (BDH Chemicals, Poole, Dorset, BH12 4NN, U.K.) using the method of Galfre et al. (1977). Hybridomas were plated in Costar dishes (Costar, Cambridge, Mass., USA) on feeder layers of mouse peritoneal exudate cells in DRPMI supplemented with 20% fetal calf serum (Gibco), and non-hybridomas selectively killed by the addition after 24 h of hypoxanthine, aminopterin and thymidine [Galfre et al., 1977].

Hybridoma supernatants were screened by immunohistology using frozen sections of human first trimester chorionic villous or decidual tissue, or term amniochorion or chorionic villous tissue. Peroxidase-conjugated rabbit anti-(mouse Ig) Ig [Sutton et al., 1986] or rabbit anti(mouse Ig)Ig and mouse anti(calf intestinal alkaline phosphatase)-alkaline phosphatase complex [Cordell et al., 1984] were used to detect antibody binding. Mouse Ig was used as a control in place of the hybridoma supernatant, and the sections were blotted with normal rabbit serum to minimise non-specific binding. Of the supernatants tested, only one hybridoma appeared to be producing an antibody specific for trophoblast, this hybridoma, now designated cell line X, was expanded, recloned by limiting dilution, and the cloned cells stored under liquid nitrogen.

Example 2

Experiments Demonstrating Specificity of the Antibody

The reactivity of the X antibody with a variety of human tissues was tested by immunohistology of frozen sections, and the results are summarised in Table 1. In first trimester tissue, antibody X reacts only with the cytotrophoblast of the cell islands and those interstitial cytotrophoblast invading the decidual tissue. It does not react with the villous cytotrophoblast, nor with the syncytiotrophoblast. The stromal cells of the chorionic villous tissue and the maternal decidua were negative. In amniochorion, either at term or from 12 weeks gestational age, antibody X labelled a sub-population of the chorionic cytotrophoblast mainly on the maternal side of the chorion. This is in contrast to NDOG2 or H317, which recognise placental alkaline phosphatase [Stirrat et al., 1983; Bulmer & Johnson, 1985], B7/21 an antibody to HLA-DP class II antigen [Starkey, 1987], H315 and HMFG1, an antibody to human milk fat globule protein [Bulmer & Johnson, 1985], all of which stain subpopulations mainly on the fetal side of the chorion. In term chorionic villous tissue, neither syncytiotrophoblast nor stromal cells were labelled by antibody X, though interstitial trophoblast were. The antibody also failed to label a variety of normal or malignant adult tissues (see Table 1).

TABLE 1

Reactivity of antibody X with human tissues Acetone-fixed frozen cryostat sections were incubated with antibody X. Antibody binding was visualised either with peroxidase-conjugated rabbit anti(mouse Ig)Ig or with rabbit anti(mouse Ig)Ig followed by a preformed complex of mouse anti(calf intestinal alkaline phosphatase) - calf intestinal alkaline phosphatase, details in text. (−) indicates no labelling, (+/−) indicates some cells labelled, and (+) indicates all cells labelled.

| Tissue | Reaction with antibody X |
|---|---|
| First trimester chorionic villous tissue | |
| syncytiotrophoblast | − |
| villous cytotrophoblast | − |
| cytotrophoblast cell islands | + |
| interstitial cytotrophoblast | + |
| stromal cells | − |
| First trimester decidua | − |
| Term chorionic villous tissue | |
| syncytiotrophoblast | − |
| stromal cells | − |
| interstitial cytotrophoblast | + |
| Term amniochorion | |
| amnion | − |
| chorionic cytotrophoblast | +/− |
| decidua | − |
| Adult tissue | |
| liver | − |
| kidney | − |
| tonsil | − |
| thymus | − |
| spleen | − |
| lung | − |
| heart | − |
| skin | − |
| Malignant cells | |
| breast carcinoma | − |
| cervical carcinoma | − |

The X antibody thus appears to recognise an antigen which is expressed only on a limited subset of human extra-villous cytotrophoblast. In first trimester tissue, antibody X labels cytotrophoblast of the cell islands, and those interstitial cytotrophoblast invading the maternal decidua. Both of these are believed to be derived from the invasive cell columns, though they differ in proliferative activity and probably in function; with the interstitial cytotrophoblast being invasive and proliferative and the cell islands demonstrating no proliferative activity, and probably having a secretory function [Dearden & Ockleford, 1983]. Antibody X does not label the subsyncytial villous trophoblast, unlike B7/21 [Starkey, 1987] and 18B/A5 [Loke & Day, 1984] which label both the extra-villous and villous cytotrophoblast in the first trimester. Antibody X also labels a subset of chorionic extra-villous cytotrophoblast, though not the same subset as that labelled by most other anti-trophoblast antibodies.

Example 3

Identification of the Antigen

Whole cellular extracts and medium conditioned by growth of the extracts/cells (to detect secreted antigen) were prepared from the choriocarcinoma cell lines, BeWo, JEG and Jar (from the American Type Culture Collection, 12301 Parklawn Drive, Rockville, Md. 20852) and from the chorionic villi of normal women (collected from the Planned Parenthood Clinic, San Francisco). The extracts (20 µl) and conditioned medium (20 µl) were analysed by polyacrylamide gel electrophoresis under reducing conditions (10% mini-gel with a 5% stacking gel run at 10 mA for 5 hours or until the dye front was 1 cm above the bottom of the tank), soaked in transfer buffer (50% methanol: 50% phosphate buffered saline pH 7.4) for one hour and transferred to nitrocellulose filters (Biorad, transblot) overnight. These western blots were incubated in blocking reagent (5% non-fat milk [Carnation], 0.1% Tween 20 [Biorad 171-6531] and 0.010% antifoam A [Sigma A 5758]) for one hour then incubated in 4ml of antibody X (undiluted hybridoma supernatant) for one hour. Blots were washed in phosphate buffered saline containing 0.1% Tween 20 four times and incubated in a peroxidase-conjugated goat anti-mouse antibody (Jackson Laboratories 115-035-146, diluted 1/1000) for one 15 hour. The blots were washed as described above, developed using the Enhanced Chemiluminescence (ECL) kit (RPN 2106, Amersham International, UK) for 60 seconds and then wrapped in Saran wrap. On exposure to autoradiographic film (Hyperfilm, Amersham, UK) for 1 minute a 100 kD band was visible only in the lane corresponding to conditioned medium of the BeWo choriocarcinoma cell line. The antibody did not react with samples of either cellular extracts or the conditioned medium of chorionic villi isolated from tissue of the same origin from normal women.

Example 4

Isolation Protocol for Isolating the Antigen

Antibody X is of the IgG2a isotype. As demonstrated in Example 3, the antigen is secreted by the choriocarcinoma cell line, BeWo, so there is a readily accessible source of antigen. Large volumes of both antibody and BeWo cell culture medium have been grown up. The first step is to prepare an immunoaffinity column. The antibody supernatant will be poured down a Protein A Sepharose column and the Fc portion of the antibody cross linked to it. After several washing steps the antigen will be introduced onto the column. The antibody will capture the antigen and form a complex. Unbound antigen and extraneous protein will be washed out and then the bound antigen eluted by adjusting the pH (reducing it to pH 2.9). The pure preparation of antigen will be run out on a conventional silver-stained protein gel to confirm that there is only one band present (i.e. no contamination proteins) and then cut out of the gel and sent to an amino acid sequencing lab. Once the amino acid sequence has been established, a series of cDNA probes will be made and used to probe a cDNA library. This will give the gene sequence of the antigen. All of the techniques required for this protocol are standard techniques which are in common use in research laboratories.

REFERENCES

Boyd, J. D. and Hamilton, W. J. (1970). The Human Placenta. Heffer and Sons, Cambridge.

Bulmer, J. N. and Johnson, P. M. (1985). Antigen expression by trophoblast populations in the human placenta and their possible immunobiological relevance. Placenta 6: 127–140.

Cordell, J. L., Falini, B., Erber, W. N., Ghosh, A. K., Abdulaziz, Z., MacDonald, S., Pulford, K. A. F., Stein, H. and Mason, D. Y. (1984). Immunoenymatic labelling of monoclonal antibodies using immune complexes of alkaline phosphatase and monoclonal anti-alkaline phosphatase (APAAP) complexes. J. Histochem. Cytochem. 32: 219–229.

Dearden, L. and Ockleford, C. D. (1983). Structure of human trophoblast: correlation with function. In: Biology of trophoblast (Loke, Y. W. & Whyte, A., eds.) pp. 69–110, Elsevier, Amsterdam, New York and Oxford.

Galfre, G., Howie, S. C., Milstein, C., Butcher, G. W. and Howard, J. C. (1977). Antibodies to major histocompatibility antigens produced by hybrid cell lines. Nature 266: 550–552.

Loke, Y. W. and Day, S. (1984). Monoclonal antibody to human cytotrophoblast. Am. J. Reprod. Immunol. 5: 106–108.

Loke, Y. W., Hsi, B. -L., Bulmer, J. N., Grivaux, C., Hawley, S., Gardner, L., King, A. and Carter, N. P. (1992). Evaluation of a monoclonal antibody, BC-1, which identifies an antigen expressed on the surface membrane of human extra-villous trophoblast. Am. J. Reprod. Immunol. 27: 77–81.

Mueller, U. W., Hawes, Catherine, S., and Jones, W. R. (1987). Identification of extra-villous trophoblast cells in human decidua using an apparently unique murine monoclonal antibody to trophoblast. Histochem. Journal 19: 288–296.

Pijnenborg, R., Dixon, G., Robertson, W. B. and Brosens, I. (1980): Trophoblastic invasion of human decidua from 8 to 18 weeks of pregnancy. Placenta 1: 3–19.

Redman, C. W. G., McMichael, A. J., Stirrat, G. M., Sunderland, C. A. and Ting, A. (1984). Class 1 major histocompatibility complex antigens on human extra-villous trophoblast. Immunology 52: 457–468.

Shorter, S. C. (1990). The isolation and characterisation of human cytotrophoblast. D. Phil. thesis, University of Oxford.

Starkey, P. M. (1987). Reactivity of human trophoblast with an antibody to the HLA class II antigen, HLA-DP. J. Reprod. Immunol. 11: 63–70.

Stirrat, G. M., Sunderland, C. A. and Redman, C. W. G. (1984). In: Obstetrics and Gynaecology Annual (Wyn, R. N., ed.) Vol. 12, pp 43–59, Appelton-Century Crofts, Connecticut, U.S.A.

Sutton, L., Gadd, M., Mason, D. Y. and Redman, C. W. G. (1986). Cells bearing class II MHC antigens in the human placenta and amniochorion. Immunology 58: 23–29.

We claim:

1. The cell line ECACC 92052819 and subclones thereto which produce antibody capable of binding specifically to cytotrophoblast.

2. Monoclonal antibody produced by the cell line ECACC 92052819 and by subclones thereof as defined in claim 1.

3. An antigen binding fragment of a monoclonal antibody as claimed in claim 2, which fragment comprises one or more of the Fab fragments of the antibody molecule.

* * * * *